(12) United States Patent
Giese et al.

(10) Patent No.: US 11,471,691 B2
(45) Date of Patent: Oct. 18, 2022

(54) IMPLANTABLE MEDICAL DEVICE WITH BIOCOMPATIBLE BATTERY SHELL

(71) Applicant: Cardiac Pacemakers, Inc., St. Paul, MN (US)

(72) Inventors: Troy Anthony Giese, Blaine, MN (US); Ignacio Chi, Mahtomedi, MN (US); Michael J. Root, Lino Lakes, MN (US); Larry Michael Killeen, Elk River, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/750,647

(22) Filed: Jan. 23, 2020

(65) Prior Publication Data
US 2020/0238095 A1    Jul. 30, 2020

Related U.S. Application Data

(60) Provisional application No. 62/796,415, filed on Jan. 24, 2019.

(51) Int. Cl.
 *A61N 1/375*    (2006.01)

(52) U.S. Cl.
 CPC ......... *A61N 1/3758* (2013.01); *A61N 1/3754* (2013.01)

(58) Field of Classification Search
None
See application file for complete search history.

(56) References Cited

U.S. PATENT DOCUMENTS

| | | | |
|---|---|---|---|
| 4,830,940 | A | 5/1989 | Keister et al. |
| 4,964,877 | A | 10/1990 | Keister et al. |

(Continued)

FOREIGN PATENT DOCUMENTS

| | | |
|---|---|---|
| EP | 2435135 | 4/2014 |
| WO | 2016140873 | 9/2016 |
| WO | 2020154486 | 7/2020 |

OTHER PUBLICATIONS

"International Search Report and Written Opinion," for PCT Application No. PCT/US2020/014763 dated Apr. 17, 2020 (15 pages).

(Continued)

*Primary Examiner* — Brian T Gedeon
(74) *Attorney, Agent, or Firm* — Pauly, DeVries Smith & Deffner LLC (57) ABSTRACT

Embodiments herein relate to implantable medical devices including a power subunit with a first biocompatible electrically conductive shell configured for direct contact with an in vivo environment. In some embodiments a lithium anode can be disposed within the first biocompatible electrically conductive shell in direct electrical communication with a feedthrough pin, wherein the feedthrough pin is electrically isolated from the first biocompatible electrically conductive shell. A cathode can also be disposed within the first biocompatible electrically conductive shell and can be in direct electrical communication with the first biocompatible electrically conductive shell. The first biocompatible electrically conductive shell has a positive electrical potential. The implantable medical device further includes an electronics control subunit with a control circuit disposed within a second biocompatible electrically conductive shell. Other embodiments are included herein.

19 Claims, 10 Drawing Sheets

(56) References Cited

U.S. PATENT DOCUMENTS

| | | | |
|---|---|---|---|
| 5,667,910 | A | 9/1997 | Takeuchi et al. |
| 6,491,639 | B1 * | 12/2002 | Turcott ................ A61B 5/0205 |
| | | | 600/508 |
| 7,005,214 | B2 | 2/2006 | Takeuchi et al. |
| 7,211,349 | B2 | 5/2007 | Leising et al. |
| 7,927,737 | B2 | 4/2011 | Scott et al. |
| 8,268,466 | B2 | 9/2012 | Takeuchi et al. |
| 8,359,098 | B2 | 1/2013 | Lund et al. |
| 8,541,131 | B2 | 9/2013 | Lund et al. |
| 9,220,911 | B2 | 12/2015 | Gordon et al. |
| 2004/0029005 | A1 | 2/2004 | Leising et al. |
| 2007/0233195 | A1 * | 10/2007 | Wahlstrand ......... H01M 50/538 |
| | | | 607/2 |
| 2008/0221629 | A1 | 9/2008 | Morgan et al. |
| 2010/0305653 | A1 | 12/2010 | Lund et al. |
| 2011/0133699 | A1 * | 6/2011 | Howard ............ H01M 10/0525 |
| | | | 320/137 |
| 2013/0196214 | A1 | 8/2013 | Scott et al. |
| 2015/0073247 | A1 | 3/2015 | Gordon et al. |
| 2017/0317331 | A1 | 11/2017 | Vedoy |
| 2018/0015290 | A1 | 1/2018 | Deininger et al. |

OTHER PUBLICATIONS

"Communication Pursuant to Rules 161(1) and 162 EPC," for EP Application No. 20706924.6, dated Aug. 31, 2021, 3 pages.
"International Preliminary Report on Patentability," for PCT Application No. PCT/US2020/014763 dated Aug. 5, 2021 (10 pages).

* cited by examiner

IMPLANTABLE MEDICAL DEVICE WITH BIOCOMPATIBLE BATTERY SHELL

This application claims the benefit of U.S. Provisional Application No. 62/796,415, filed Jan. 24, 2019, the content of which is herein incorporated by reference in its entirety.

FIELD

Embodiments herein relate to implantable medical devices including a power subunit with a first biocompatible electrically conductive shell configured for direct contact with an in vivo environment.

BACKGROUND

Implantable medical devices are now commonly used for monitoring a patient's condition and in some cases also administering therapy to the patient. In some cases, the implantable medical device may be implanted only temporarily. In other cases, the implantable medical device may be implanted chronically over a period of years.

In general, it can be desirable to minimize the size of a device to be implanted in the body. Reduced size can boost patient comfort as well as allow for greater placement site and placement method flexibility. As a result, there is a general trend towards smaller and smaller devices over time. For example, state-of-the-art pacemakers are typically much smaller today than the pioneering devices of decades past. Reduced size has been made possible through advancements in the materials and component parts of devices as well as refinements of overall designs.

SUMMARY

Embodiments herein relate to implantable medical devices including a power subunit with a first biocompatible electrically conductive shell configured for direct contact with an in vivo environment. In a first aspect, an implantable medical device is included having a power subunit with a first biocompatible electrically conductive shell configured for direct contact with an in vivo environment. A lithium anode is disposed within the first biocompatible electrically conductive shell in direct electrical communication with a feedthrough pin, wherein the feedthrough pin is electrically isolated from the first biocompatible electrically conductive shell. A cathode is disposed within the first biocompatible electrically conductive shell and in direct electrical communication with the first biocompatible electrically conductive shell. The implantable medical device further includes an electronics control subunit including a second biocompatible electrically conductive shell configured for direct contact with an in vivo environment. A control circuit is disposed within the second biocompatible electrically conductive shell. The power subunit is coupled to the electronics control subunit and the power subunit is in electrical communication with the electronics control subunit. The first biocompatible electrically conductive shell has a positive electrical potential.

In a second aspect, in addition to one or more of the preceding or following aspects, or in the alternative to some aspects, the first biocompatible electrically conductive shell and the second biocompatible electrically conductive shell can be titanium or a titanium alloy.

In a third aspect, in addition to one or more of the preceding or following aspects, or in the alternative to some aspects, the first biocompatible electrically conductive shell can have machined surfaces.

In a fourth aspect, in addition to one or more of the preceding or following aspects, or in the alternative to some aspects, the first biocompatible electrically conductive shell can have stamped surfaces.

In a fifth aspect, in addition to one or more of the preceding or following aspects, or in the alternative to some aspects, the first biocompatible electrically conductive shell includes an exterior surface for contact with an in vivo environment and the implantable medical device further includes a polymeric coating disposed over at least a portion of the exterior surface of the first biocompatible electrically conductive shell.

In a sixth aspect, in addition to one or more of the preceding or following aspects, or in the alternative to some aspects, the polymeric coating can be a parylene coating.

In a seventh aspect, in addition to one or more of the preceding or following aspects, or in the alternative to some aspects, the first biocompatible electrically conductive shell can have a thickness of 0.006 to 0.012 inches.

In an eighth aspect, in addition to one or more of the preceding or following aspects, or in the alternative to some aspects, the first biocompatible electrically conductive shell has perimeter dimensions that is less than 5 percent different than the second biocompatible electrically conductive shell.

In a ninth aspect, in addition to one or more of the preceding or following aspects, or in the alternative to some aspects, the first biocompatible electrically conductive shell and the second biocompatible electrically conductive shell are welded together.

In a tenth aspect, in addition to one or more of the preceding or following aspects, or in the alternative to some aspects, the first biocompatible electrically conductive shell of the power subunit has an electrical potential of 2.5 V vs. lithium to 3.5 V vs. lithium.

In an eleventh aspect, an implantable medical device is included having a power subunit with a first biocompatible electrically conductive shell configured for direct contact with an in vivo environment. A lithium anode can be disposed within the first biocompatible electrically conductive shell in direct electrical communication with a first feedthrough pin, wherein the first feedthrough pin is electrically isolated from the first biocompatible electrically conductive shell. A cathode can be disposed within the first biocompatible electrically conductive shell and in direct electrical communication with a second feedthrough pin, wherein the second feedthrough pin is electrically isolated from the first biocompatible electrically conductive shell. The device can further include an electronics control subunit including a second biocompatible electrically conductive shell configured for direct contact with an in vivo environment and a control circuit disposed within the second biocompatible electrically conductive shell. The power subunit can be coupled to the electronics control subunit and the power subunit can be in electrical communication with the electronics control subunit. The first biocompatible electrically conductive shell can have an electrical potential of between 0 V vs. lithium and 3 V vs. lithium.

In a twelfth aspect, in addition to one or more of the preceding or following aspects, or in the alternative to some aspects, wherein the first biocompatible electrically conductive shell has an electrical potential of between 0.2 to 0.5 V vs. lithium.

In a thirteenth aspect, in addition to one or more of the preceding or following aspects, or in the alternative to some aspects, the first biocompatible electrically conductive shell includes machined surfaces.

In a fourteenth aspect, in addition to one or more of the preceding or following aspects, or in the alternative to some aspects, the first biocompatible electrically conductive shell included stamped surfaces.

In a fifteenth aspect, in addition to one or more of the preceding or following aspects, or in the alternative to some aspects, the first biocompatible electrically conductive shell can have a thickness of 0.006 to 0.012 inches.

In a sixteenth aspect, an implantable medical device is included having a power subunit including a first biocompatible electrically conductive shell configured for direct contact with an in vivo environment. A lithium anode can be disposed within the first biocompatible electrically conductive shell in direct electrical communication with a first feedthrough pin, wherein the first feedthrough pin is electrically isolated from the first biocompatible electrically conductive shell. A cathode can be disposed within the first biocompatible electrically conductive shell and in direct electrical communication with a second feedthrough pin, wherein the second feedthrough pin is electrically isolated from the first biocompatible electrically conductive shell. An electronics control subunit can be included and can have a second biocompatible electrically conductive shell configured for direct contact with an in vivo environment and a control circuit disposed within the second biocompatible electrically conductive shell. The power subunit can be coupled to the electronics control subunit and the power subunit and can be in electrical communication with the electronics control subunit. The electronic control subunit can include a negative bias output pin. The implantable medical device can further include an electrical conductor providing electrical communication between the negative bias output pin and the first biocompatible electrically conductive shell. The first biocompatible electrically conductive shell can have an electrical potential greater than 0.001 V vs lithium and less than 3.0 V vs lithium.

In a seventeenth aspect, in addition to one or more of the preceding or following aspects, or in the alternative to some aspects, the first biocompatible electrically conductive shell can have an electrical potential greater than 0.1 V vs lithium and less than 3.0 V vs lithium.

In an eighteenth aspect, in addition to one or more of the preceding or following aspects, or in the alternative to some aspects, the first biocompatible electrically conductive shell can have machined surfaces.

In a nineteenth aspect, in addition to one or more of the preceding or following aspects, or in the alternative to some aspects, the first biocompatible electrically conductive shell can include an exterior surface for contact with an in vivo environment and a polymeric coating can be disposed over a portion of the exterior surface of the first biocompatible electrically conductive shell.

In a twentieth aspect, in addition to one or more of the preceding or following aspects, or in the alternative to some aspects, the first biocompatible electrically conductive shell can have a thickness of 0.006 to 0.012 inches.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

While there is a general trend across many implanted medical devices towards reduced size, there is still more room inside of the housing (sometimes referred to as a "can") of some types of devices to place components and less room in other types of devices. In general, dedicated implantable monitoring devices can serve as an example of a type of device where there is very little room within the housing to place components.

In many cases, implantable medical devices are powered and contain a battery to provide such power. In devices where there is more internal room, a battery or cell having its own discrete case or shell can be placed therein. In this configuration, because the housing or shell of the battery is physically separate from and internal to the housing or shell of the overall device, the degree of biocompatibility of the battery housing matters less allowing the selection of materials based on factors such as manufacturing ease and cost.

In accordance with various embodiments herein, the housing or shell of the battery is configured for direct contact with the in vivo environment. As such, the housing or shell of the battery is formed of an electrically conductive biocompatible material, such as a biocompatible metal.

The in vivo environment contains a complex mixture of components including salts, ions, acids, and the like. If the anode of the battery is in direct electrical contact with the housing or shell of the implanted device, then the housing or shell will have a relatively negative electrical potential. While not intending to be bound by theory, such a negative electrical potential can attract positively charged ions to the surface of the housing or shell, particularly if the negative electrical potential is significant. In addition, designs without a significantly negative electrical potential at the housing or shell may allow for additional flexibility in the selection of specific materials and structural designs for the device components.

However, in accordance with various embodiments herein, the housing or shell can have a neutral electrical potential or a positive electrical potential. The housing or shell can be configured to have a neutral electrical potential by isolating both the cathode and anode from the housing or shell. In other embodiments, the housing or shell can be configured to have a positive electrical potential by placing the cathode of the battery or electrochemical cell in direct electrical communication with the housing or shell.

In some embodiments, the housing or shell can be configured to have a negative electrical potential but reduced in magnitude compared with a configuration where the anode is in directed electrical communication with the housing or shell. For example, both the anode and cathode of the electrochemical cell can be isolated from the housing or shell using feedthrough structures or the like, but an electrical conductor can provide electrical communication between the housing or shell and a negative bias output pin associated with the circuitry in the electronics control subunit in order to provide the housing or shell with a relative negative electrical potential at a reduced magnitude.

Figure 1:
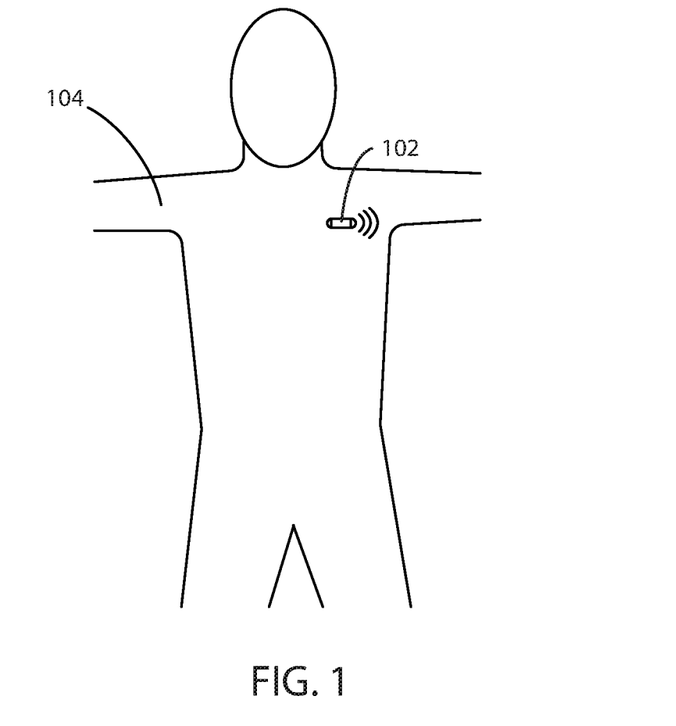
FIG. 1 is a schematic view of an implantable medical device implanted within a patient in accordance with various embodiments herein.

Referring now to FIG. 1, a schematic view is shown of an implantable medical device 102 implanted within a patient 104 in accordance with various embodiments herein. In various embodiments, at least a portion of the medical device system can be implantable. In some embodiments, the implantable medical device 102 can include an implantable loop recorder, implantable monitor device, or the like. In some embodiments, the entire implantable medical device 102 can be implanted within the body of a patient 104. Various implant sites can be used including areas on the limbs, the upper torso, the abdominal area, and the like. In some embodiments, the implantable medical device 102 can be implanted subcutaneously. In some embodiments, the medical device system can include one or more additional medical devices that are communicatively coupled to one another.

Figure 2:
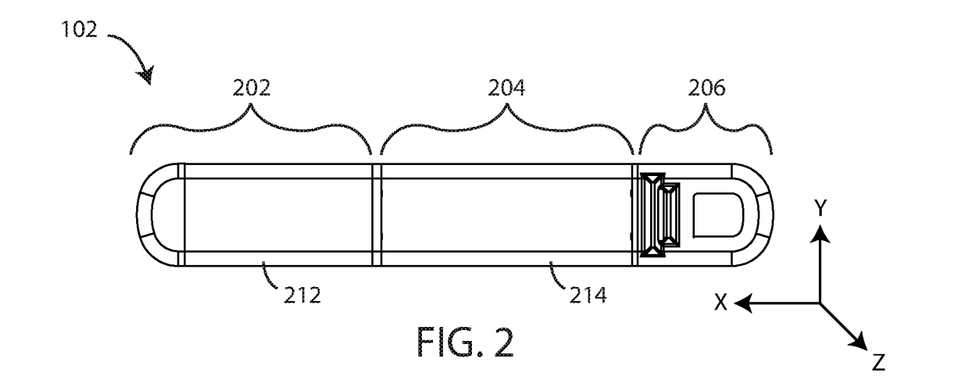
FIG. 2 is a schematic view of an implantable medical device in accordance with various embodiments herein.

Referring now to FIG. 2, a schematic view of an implantable medical device 102 is shown in accordance with various embodiments herein. The implantable medical device 102 can include a power subunit 202, an electronics control subunit 204, and a wireless communications subunit 206. The power subunit 202 can include components of an electrochemical cell. The power subunit 202 can include a first biocompatible electrically conductive shell 212 configured for direct contact with an in vivo environment. The electronics control subunit 204 can include electronic components to control operations of the device including, for example, a controller or control circuit. The electronics control subunit 204 can include a second biocompatible electrically conductive shell 214 configured for direct contact with an in vivo environment.

The power subunit 202 can be coupled to the electronics control subunit 204. In some embodiments, the power subunit 202 can be welded to the electronics control subunit 204. Welding can be performed using various techniques including laser welding. In various embodiments, the first biocompatible electrically conductive shell of the power subunit has about the same cross-sectional perimeter dimensions as the second biocompatible electrically conductive shell of the electronics control subunit. In various embodiments, the first biocompatible electrically conductive shell of the power subunit has cross-sectional perimeter dimensions that are less than 5% different than that of the second biocompatible electrically conductive shell of the electronics control subunit.

The implantable medical device 102 can have various dimensions. The overall length (X axis) can be greater than or equal to 1, 3, 5, 7, 9, 10, 12, 14, 16, 18, or 20 mm. In some embodiments, the length can be less than or equal to 80, 74, 68, 62, 56, 50, 44, 38, 32, 26, or 20 mm. In some embodiments, the length can fall within a range of 1 to 80 mm, or 3 to 74 mm, or 5 to 68 mm, or 7 to 62 mm, or 9 to 56 mm, or 10 to 50 mm, or 12 to 44 mm, or 14 to 38 mm, or 16 to 32 mm, or 18 to 26 mm, or can be about 20 mm. The overall width (Y axis) can be greater than or equal to 1.0 mm, 1.8 mm, 2.5 mm, 3.2 mm, or 4.0 mm. In some embodiments, the width can be less than or equal to 15.0 mm, 12.2 mm, 9.5 mm, 6.8 mm, or 4.0 mm. In some embodiments, the width can fall within a range of 1.0 mm to 15.0 mm, or 1.8 mm to 12.2 mm, or 2.5 mm to 9.5 mm, or 3.2 mm to 6.8 mm, or can be about 4.0 mm.

The overall depth (Z axis) can be greater than or equal to 1.0 mm, 1.8 mm, 2.5 mm, 3.2 mm, or 4.0 mm. In some embodiments, the depth can be less than or equal to 15.0 mm, 12.2 mm, 9.5 mm, 6.8 mm, or 4.0 mm. In some embodiments, the depth can fall within a range of 1.0 mm to 15.0 mm, or 1.8 mm to 12.2 mm, or 2.5 mm to 9.5 mm, or 3.2 mm to 6.8 mm, or can be about 4.0 mm.

Figure 3:
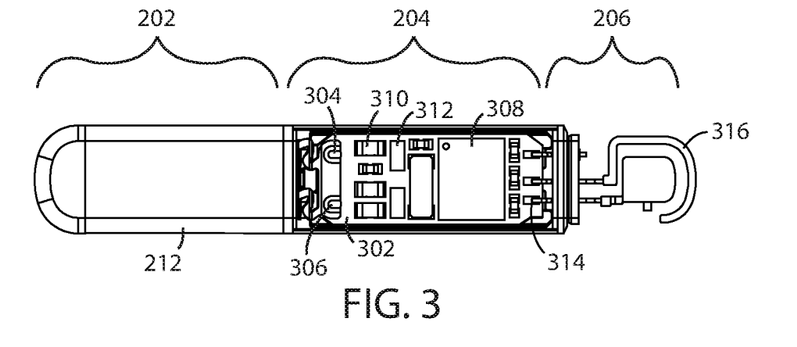
FIG. 3 is a schematic view of an implantable medical device in accordance with various embodiments herein.

Referring now to FIG. 3, a schematic view of an implantable medical device 102 is shown in accordance with various embodiments herein. In this view, the electrically conductive shell 214 has been removed to show the components within the electronics control subunit 204 of the implantable medical device. The electronics control subunit 204 can include a circuit board 302 and power input connections 304, 306 which can be in electrical communication with output pins of the power subunit 202. The electronics control subunit 204 can further include a controller 308 which can form part of a control circuit. The electronics control subunit 204 can further circuit components 310 and 312. It will be appreciated that many different circuit components can be included such as integrated circuits of various types, signal processing chips, ASICs (application specific integrated circuits), clock circuits, capacitors, and the like. The electronics control subunit 204 can also include I/O pins 314. The total number of I/O pins (digital or analog) is not particularly limited. The wireless communications subunit 206 can include an antenna 316, which can be in electrical communication with I/O pins 314. In some embodiments, one of the I/O pins 314 can be a negative bias output pin, which can be regulated to provide a relative negative electrical potential.

Figure 4:
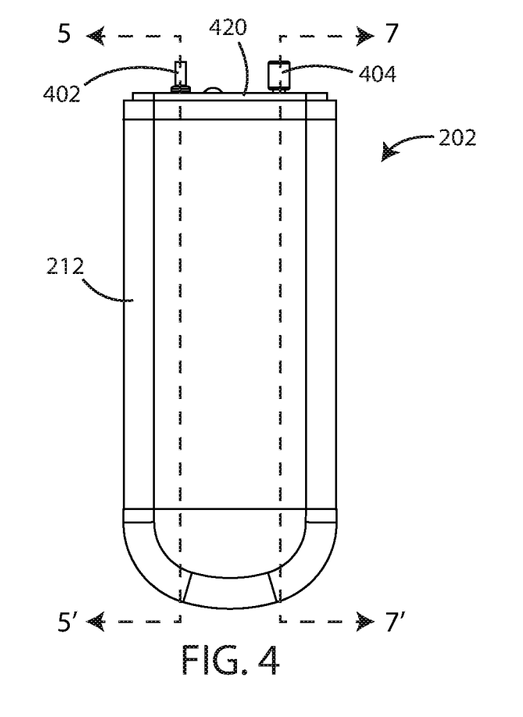
FIG. 4 is a power subunit in accordance with various embodiments herein.

Referring now to FIG. 4, a power subunit 202 is shown in accordance with various embodiments herein. The power subunit 202 can include electrically conductive shell 212. The power subunit 202 can further include a lid 420, which can be attached (such as by welding or another technique) to the electrically conductive shell 212. The power subunit 202 can further include a cathode pin 402 and an anode pin 404. Cathode pin 402 and anode pin 404 can be formed of various conductive materials such as metals. In some embodiments, the cathode pin 402 and/or the anode pin 404 are formed of molybdenum or a molybdenum containing alloy. However, many different pin materials are contemplated herein.

Case Positive Configuration

In various embodiments, the implantable medical device can be configured so that the biocompatible electrically conductive shell 212 of the power subunit 202 and/or electrically conductive shell of the electronics control subunit 204 has a relative positive electrical potential. By way of example, the implantable medical device can be configured so that the electrically conductive shell 212 has an electrical potential of greater than or equal to 2.0, 2.1, 2.2, 2.3, 2.4, 2.5, 2.6, 2.7, 2.8, 2.9, 3.0, 3.1, 3.2, 3.3, 3.4, or 3.5 volts vs. lithium. In some embodiments, the electrical potential can be less than or equal to 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, or 2.8 volts vs. lithium. In some embodiments, the electrical potential can fall within a range of 2.0 to 5.0 volts, or 2.1 to 4.9 volts, or 2.2 to 4.8 volts, or 2.3 to 4.7 volts, or 2.4 to 4.6 volts, or 2.5 to 4.5 volts, or 2.5 to 3.5 volts, or 2.6 to 4.4 volts, or 2.7 to 4.3 volts, or 2.8 to 4.2 volts, or 2.9 to 4.1 volts, or 3.0 to 4.0 volts, or 3.1 to 3.9 volts, or 3.2 to 3.8 volts, or 3.3 to 3.7 volts, or 3.4 to 3.6 volts, or can be about 3.5 volts vs. lithium.

Figure 5:
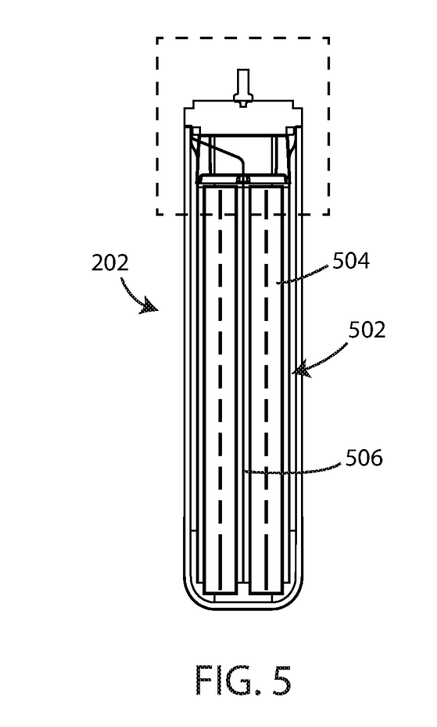
FIG. 5 is a cross-sectional view of a power subunit as taken along line 5-5' of FIG. 4 in accordance with various embodiments herein.
Figure 6:
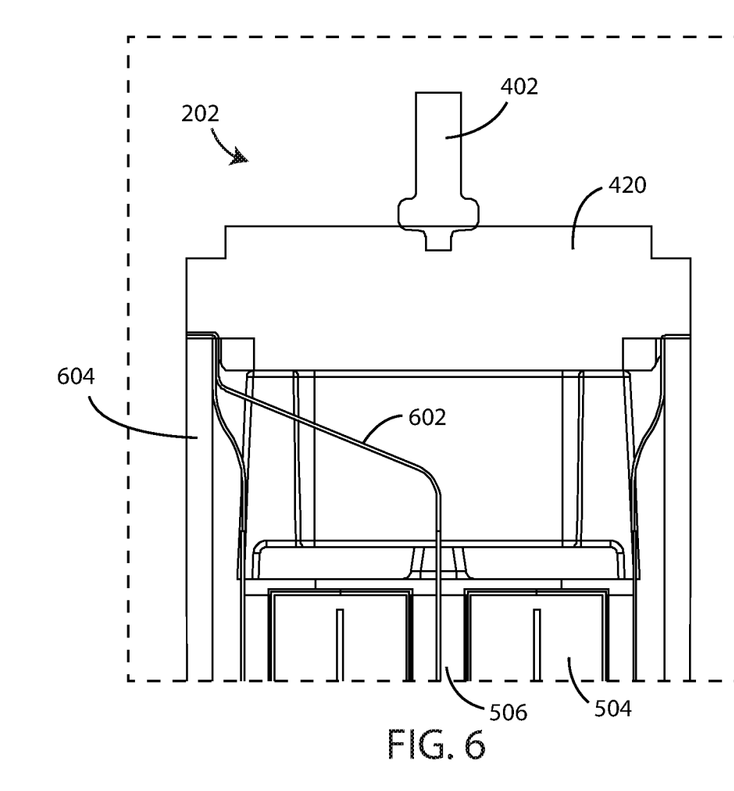
FIG. 6 is an enlarged view of a portion of FIG. 5 in accordance with various embodiments herein.

Referring now to FIG. 5, a cross-sectional view of the power subunit 202 is shown as taken along line 5-5' of FIG. 4 in accordance with various embodiments herein. The power subunit 202 can include components of an electrochemical cell 502 including an anode 504 and a cathode 506. Referring now to FIG. 6, an enlarged view of a portion of FIG. 5 is shown in accordance with various embodiments herein. In this view, it can be seen that the power subunit 202 can include a cathode pin 402 and a lid 420. Further, a cathode connection tab 602 can provide electrical communication between the cathode 506 and the lid 420 and the shell 604 or case of the power subunit 202, thus provide the shell 604 or case with a relative positive electrical potential.

Figure 7:
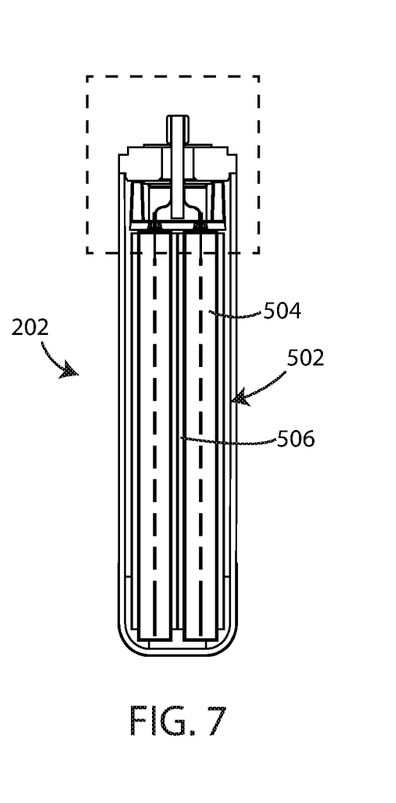
FIG. 7 is a cross-sectional view of a power subunit as taken along line 7-7' of FIG. 4 in accordance with various embodiments herein.
Figure 8:
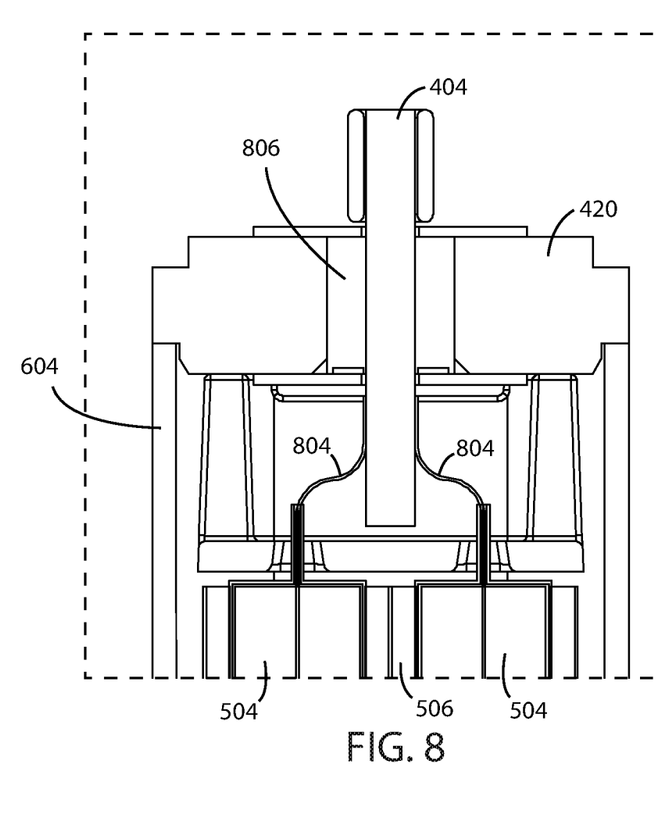
FIG. 8 is an enlarged view of a portion of FIG. 7 in accordance with various embodiments herein.

Referring now to FIG. 7, a cross-sectional view of the power subunit 202 is shown as taken along line 7-7' of FIG. 4 in accordance with various embodiments herein. Again, the power subunit 202 can include components of an electrochemical cell 502 including an anode 504 and a cathode 506. Referring now to FIG. 8, an enlarged view of a portion of FIG. 7 is shown in accordance with various embodiments herein. In this view, it can be seen that the power subunit 202 can include an anode pin 404 and a lid 420. Further, anode connection tabs 804 can provide electrical communication between the anode 504 and the anode pin 404. A feedthrough structure 806 can serve to electrically isolate the anode pin 404 from the shell 604 and case of the power subunit 202. The feedthrough structure 806 can be formed of a non-conductive material such as a non-conductive ceramic, glass, polymer, composite, or the like.

Case Neutral Configuration

In various embodiments, the implantable medical device can be configured so that the electrically conductive shell 212 of the power subunit 202 and/or electrically conductive shell of the electronics control subunit 204 has a substantially neutral electrical potential. By way of example, the implantable medical device can be configured so that the electrically conductive shell 212 has an electrical potential of greater than or equal to −0.1 volts and less than or equal to 0.1 volts, or about 0 volts.

Figure 9:
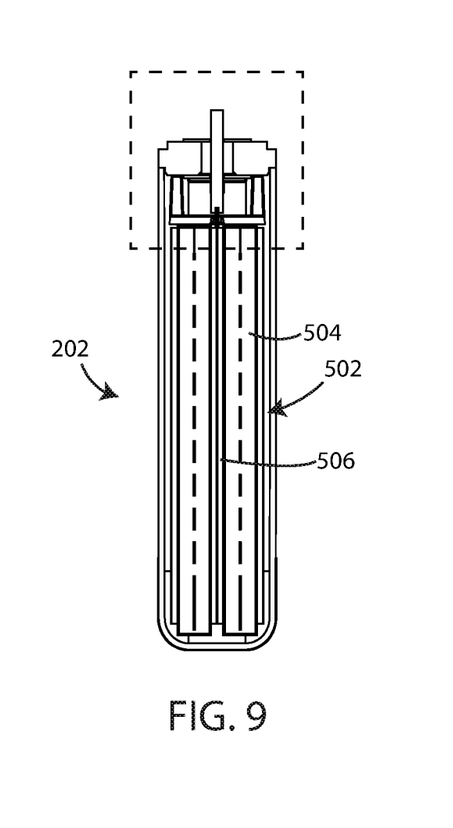
FIG. 9 is a cross-sectional view of a power subunit in accordance with an alternative construction as taken along line 5-5' of FIG. 4 in accordance with various embodiments herein.
Figure 10:
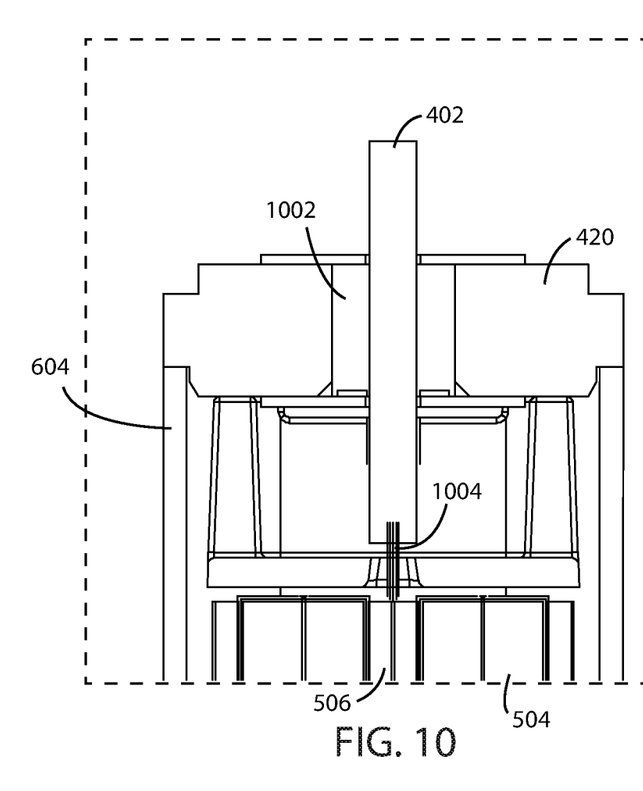
FIG. 10 is an enlarged view of a portion of FIG. 9 in accordance with various embodiments herein.

Referring now to FIG. 9, a cross-sectional view of the power subunit 202 in accordance with an alternative construction is shown as taken along line 5-5' in accordance with various embodiments herein. The power subunit 202 can include components of an electrochemical cell 502 including an anode 504 and a cathode 506. Referring now to FIG. 10, an enlarged view of a portion of FIG. 9 is shown in accordance with various embodiments herein. In this view, it can be seen that the power subunit 202 can include a cathode pin 402 and a lid 420. Further, cathode connection tab 1004 can provide electrical communication between the cathode 506 and the cathode pin 402. A feedthrough structure 1002 can serve to electrically isolate the cathode pin 402 from the shell 604 and case of the power subunit 202. In this manner, wherein the anode pin is similarly isolated from the shell 604 and the case of the power subunit 202, the shell 604 and the case can have a relative neutral electrical potential.

In various embodiments, the biocompatible electrically conductive shell 212 of the power subunit 202 and/or electrically conductive shell of the electronics control subunit 204 has a relatively neutral electrical potential In some embodiments, the electrical potential can be at least 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 V vs. lithium. In some embodiments, the electrical potential can be less than or equal to 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 V vs. lithium. In some embodiments, the electrical potential can fall within a range between any of the foregoing.

Regulated Case Negative Configuration

In various embodiments, the implantable medical device can be configured so that the electrically conductive shell 212 of the power subunit 202 and/or electrically conductive shell of the electronics control subunit 204 has a relative negative electrical potential but reduced in magnitude in comparison to the relative negative electrical potential if the electrically conductive shell were in direct electrical communication with the anode of the electrochemical cell or battery. By way of example, the implantable medical device can be configured so that the electrically conductive shell 212 has an electrical potential of greater than 0, 0.001, 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, or 2.9 V vs. lithium. In some embodiments, the electrical potential can be less than or equal to 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0 V vs. lithium. In some embodiments, the electrical potential can fall within a range between any of the foregoing.

In some embodiments, the implantable medical device can be configured so that the electrically conductive shell 212 of the power subunit 202 and/or electrically conductive shell of the electronics control subunit 204 has a relative negative electrical potential at certain times. For example, the output from a negative bias output pin or similar structure can be different at different points in time. In some embodiments, the electrically conductive shell 212 of the power subunit 202 and/or electrically conductive shell of the electronics control subunit 204 can be substantially neutral prior to implantation (or the start of the implantation process) of the device. In some embodiments, after implantation has occurred, then the electrically conductive shell 212 of the power subunit 202 and/or electrically conductive shell of the electronics control subunit 204 can have a relative negative electrical potential. Implantation (or the implantation process) can be detected based on detecting typical commands/communications associated with device initiation within a patient including, but not limited to, a wake-up or power-on command, configuration instructions associated with implantation, and the like. In some embodiments, after a specific command has been received, then the electrically conductive shell 212 of the power subunit 202 and/or electrically conductive shell of the electronics control subunit 204 can have a relative negative electrical potential.

Figure 11:
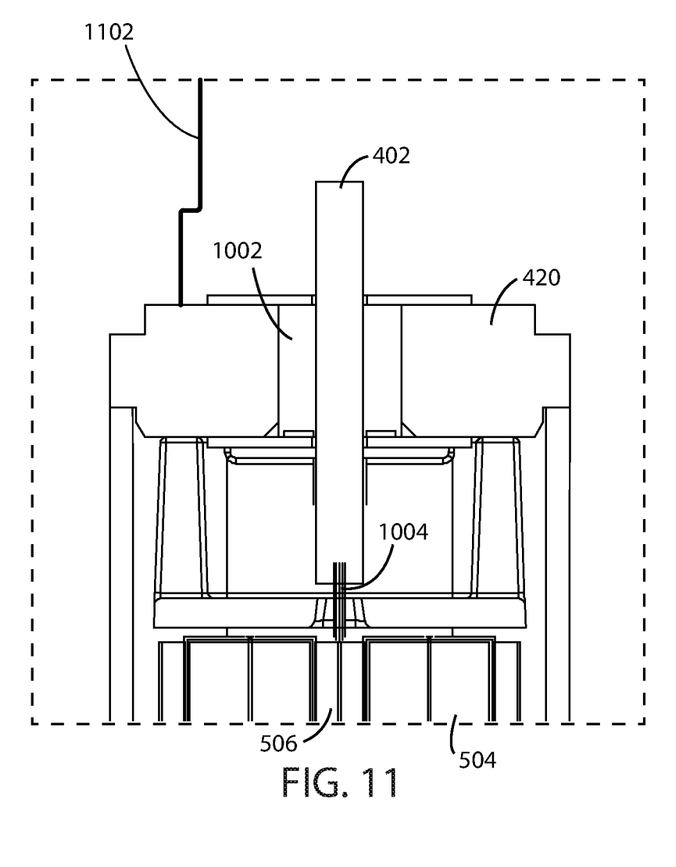
FIG. 11 is a partial cross-sectional view of a portion of an alternative construction of a power subunit in accordance with various embodiments herein.

Referring now to FIG. 11, a partial cross-sectional view of a portion of an alternative construction of a power subunit 202 is shown in accordance with various embodiments herein. In this view it can be seen that the power subunit 202 can include a cathode pin 402 and a lid 420. Further, cathode connection tab 1004 can provide electrical communication between the cathode 506 and the cathode pin 402. A feedthrough structure 1002 can serve to electrically isolate the cathode pin 402 from the shell 604 and case of the power subunit 202. However, an electrical conductor 1102 can be in electrical communication with the lid 420 and/or the shell 604. The electrical conductor 1102 can provide electrical communication between a negative bias output pin or contact located on a circuit board within the electronics control subunit 204 or on another structure therein. The negative bias output pin can have a regulated relative negative electrical potential and thus the shell 604 of the power subunit 202 can have a regulated relative negative electrical potential. It will be appreciated that although FIG. 11 shows the conductor directly contacting the lid 420, it can also directly contact the shell 604 or a component in electrical communication therewith such as the shell of the adjacent electronics control subunit 204.

Figure 12:
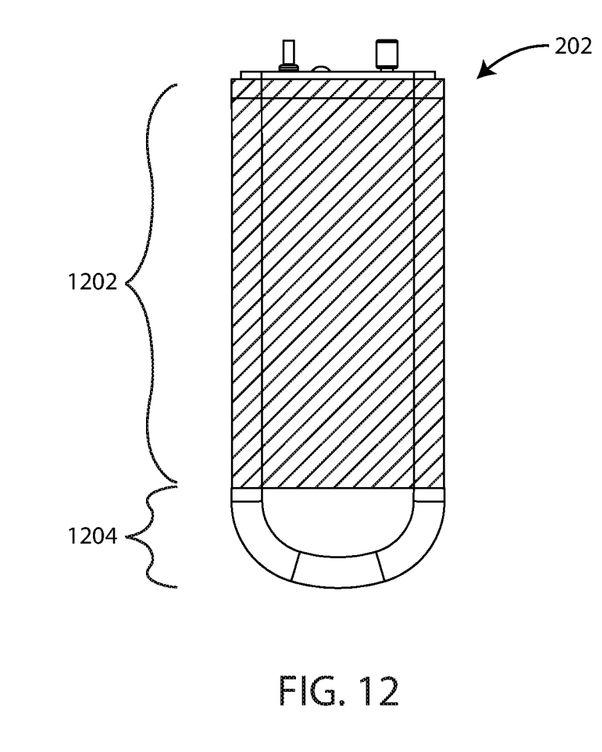
FIG. 12 is a schematic view of a power subunit in accordance with various embodiments herein.

In some embodiments, at least a portion of an exterior surface of the power subunit 202 can be covered with a polymeric material. Referring now to FIG. 12, a power subunit 202 is shown in accordance with various embodiments herein. The power subunit 202 can include electrically conductive shell 212. The power subunit 202 can further include a lid 420, which can be attached (such as by welding or another technique) to the electrically conductive shell 212. The power subunit 202 can further include a cathode pin 402 and an anode pin 404. The power subunit 202 can include a polymeric coating disposed over a portion 1202 of the exterior surface. Various polymeric coatings are contemplated herein. In some embodiments, the polymeric coating can be a vapor-deposited polymeric coating. In some embodiments, the polymeric coating can include parylene. A portion 1204 of the exterior surface of the power subunit 202 can also remain uncovered by the polymeric coating. It will be appreciated that in various embodiments the entire exterior surface can be covered, only portions of exterior surface can be covered, or the device may be completely uncovered by a polymeric coating.

Figure 13:
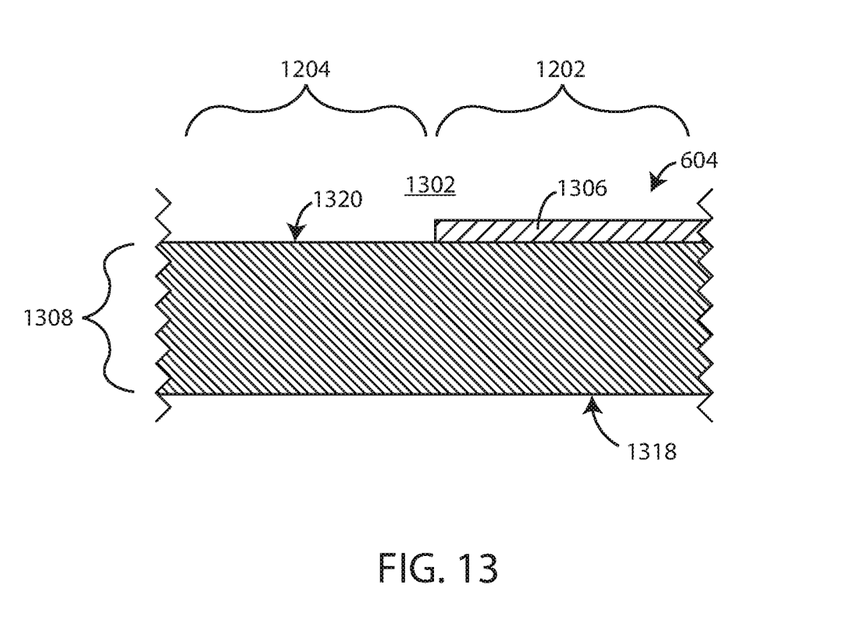
FIG. 13 is a schematic cross-sectional view of a portion of a power subunit shell in accordance with various embodiments herein.

Referring now to FIG. 13, a cross-sectional view is shown of a portion of the power subunit shell 604 in accordance with various embodiments herein. The shell 604 can include an electrically conductive biocompatible material layer 1308. Further, a polymeric coating 1306 can be disposed over a portion 1202 of the exterior surface 1320. The shell 604 can be in direct contact with the environment outside 1302 of the device, such as the in vivo environment when the device is implanted.

In some embodiments, the thickness of the electrically conductive biocompatible material layer 1308 can be greater than or equal to 0.004 inches, 0.005 inches, 0.006 inches, 0.007 inches, or 0.008 inches. In some embodiments, the electrically conductive biocompatible material layer 1308 can be less than or equal to 0.016 inches, 0.014 inches, 0.012 inches, 0.011 inches, 0.010 inches, 0.009 inches, or 0.008 inches. In some embodiments, the thickness of shell 1208 can fall within a range of 0.004 inches to 0.014 inches, 0.004 inches to 0.012 inches, or 0.005 inches to 0.011 inches, or 0.006 inches to 0.010 inches, or 0.007 inches to 0.009 inches, or can be about 0.008 inches on average (mean).

In some embodiments, the electrically conductive biocompatible material layer 1308 can be deep drawn. However, deep drawing can result in a structure with higher residual stress and a greater number of surface cracks which can serve as concentration points for stress. In some embodiments, the electrically conductive biocompatible material layer 1308 can be machined (e.g., can have machined surfaces). Machining the structure can result in reduced residual stress and fewer surface cracks. In some embodiment, the surface roughness (inside surface 1318 and/or outside surface 1320) can be less than or equal to 40, 30, 25, 20, 15, 10, or 8 µin Ra, or can be an amount falling within a range between any of the foregoing. Other techniques for forming an electrically conductive biocompatible material layer can include stamping processes, additive manufacturing processes, and the like.

The electrically conductive biocompatible material layer can be formed of various materials. In some embodiments, the electrically conductive biocompatible material layer can include a metal. In some embodiments, the electrically conductive biocompatible material layer can include one or more of titanium, titanium alloys, stainless steel, cobalt-chromium alloys, and the like.

Figure 14:
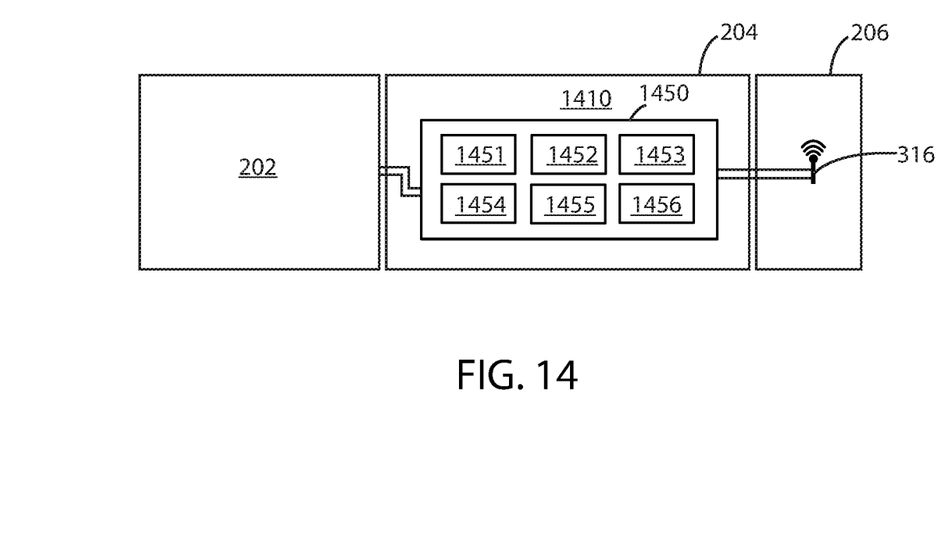
FIG. 14 is a block diagram of components of an implanted medical device in accordance with various embodiments herein.

It will be appreciated that the implantable medical device can include many different components depending on the desired functionality. Referring now to FIG. 14 a block diagram is shown of components of an implanted medical device in accordance with various embodiments herein. However, it will be appreciated that various specific embodiments can include a greater number of components, a lesser number of components, or different components. In this example, the implantable medical device 102 can include circuitry 1450. The circuitry 1450 can include various electrical components, including, but not limited to a controller 1451 (which can form part of a control circuit), a sensor 1452 (e.g., an accelerometer, a gyroscope, a microphone, a bio-impedance sensor), a microprocessor 1453, therapy unit circuitry 1454, recorder circuitry 1455, and sensor interface circuitry 1456. Other examples of components suitable for use in the medical device systems embodied herein can include telemetry circuitry, memory circuitry (e.g., such as random access memory (RAM) and/or read only memory (ROM)), power supply circuitry (which can include, but not be limited to, one or more batteries, a capacitor, a power interface circuit, etc.), normalization circuitry, control circuitry, electrical field sensor and stimulation circuitry, display circuitry, and the like.

In some embodiments, one or more components can be integrated into the implantable medical device and in other embodiments one or more components can be separate. In some embodiments recorder circuitry can record the data produced by the sensors of the device and record time stamps regarding the same. In some embodiments, the circuitry can be hardwired to execute various functions while in other embodiments, the circuitry can be implemented as instructions executing on a controller, a microprocessor, other computation device, application specific integrated circuit (ASIC), or the like.

In some embodiments, the implantable medical device 102 can include a chemical sensor. In some embodiments, the chemical sensor is an optical chemical sensor. However, in other embodiments the chemical sensor can be a potentiometric chemical sensor. The chemical sensor can specifically include at least one chemical sensing element, an optical window, and an electro-optical module. The electro-optical module can be in electrical communication with the circuitry within the interior volume 1410. In some embodiments, the chemical sensor 1420 can be configured to measure a cellular interstitial component, a blood component, or a breath component, or any analytes thereof. In some embodiments the blood component can include blood constituents or analytes thereof, such as red blood cells; white blood cells including at least neutrophils, eosinophils, and basophils; platelets; hemoglobin; and the like.

The implantable medical device 102 can include a controller 1451. In some embodiments, the controller 1451 can be configured to execute one or more operations described herein. The implantable medical device 102 can include additional components, for example, a therapy unit circuitry 1454. The therapy unit circuitry 1454 can be configured to deliver a therapy to a patient and/or control or influence the delivery of a therapy provided by another device. In some embodiments, the therapy unit can be configured to provide optimum therapy to a patient depending on if they are in a recumbent, standing or sitting position. Examples of therapies can include, but are not limited to, pacing schemes such as rate-adaptive pacing, cardiac-resynchronization therapy (CRT), delivery of a neurostimulation therapy, administration of therapeutic agents, and the like. In some embodiments, the therapy unit circuitry 1454 can be a pharmaceutical therapy unit. In some embodiments, the therapy unit circuitry 1454 can include both an electrical therapy unit and a pharmaceutical therapy unit. In some embodiments, the therapy unit circuitry 1454 can be directed by the controller 1451 to deliver a therapy to a patient.

Figure 15:
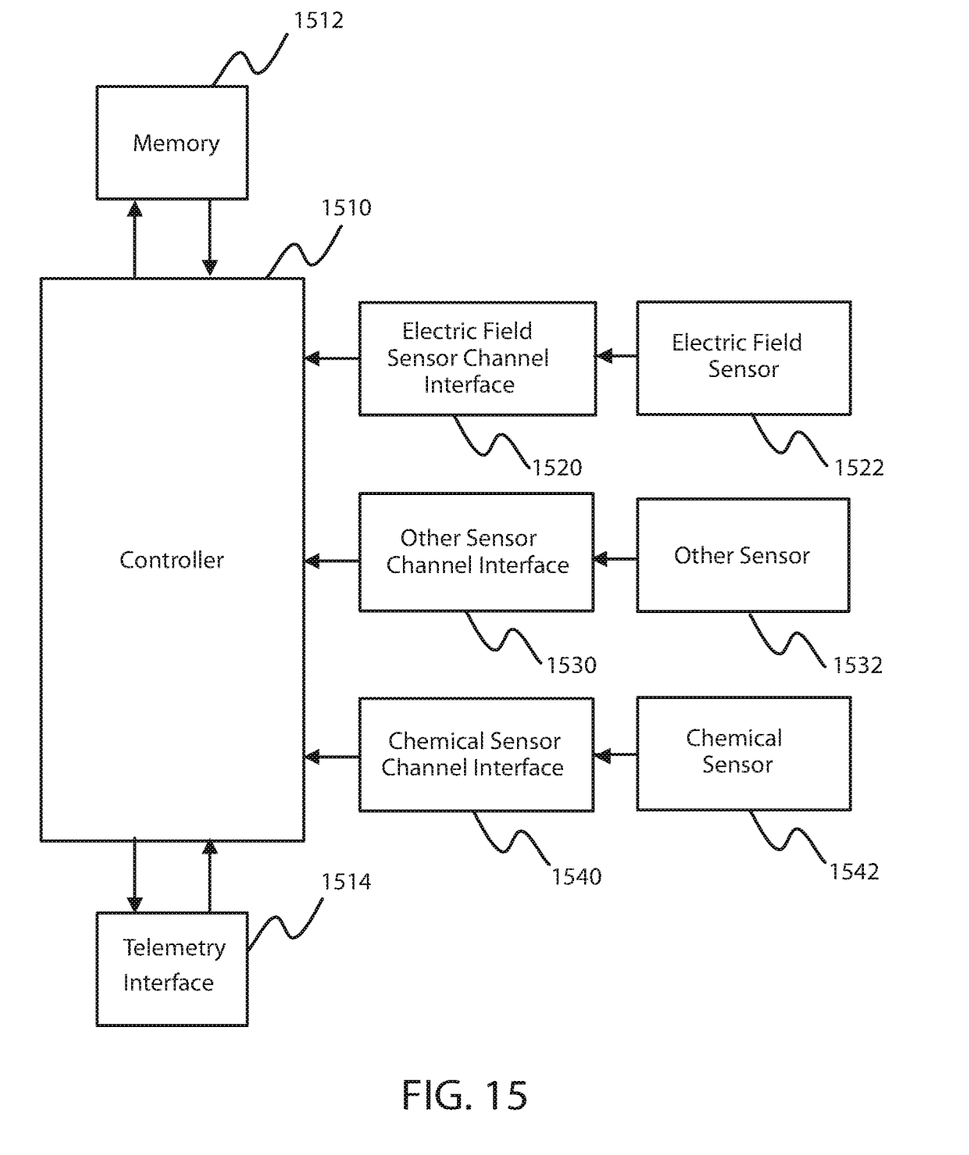
FIG. 15 is a schematic diagram of components of an implantable medical device in accordance with various embodiments herein.

Referring now to FIG. 15 is a schematic diagram of components of an implantable medical device in accordance with various embodiments herein. Elements of some embodiments of a medical device system are shown in FIG. 15 in accordance with the embodiments herein. However, it will be appreciated that some embodiments can include additional elements beyond those shown in FIG. 15. In addition, some embodiments may lack some elements shown in FIG. 15. The medical device, as embodied herein, can gather information through one or more sensing channels 1520, 1530, 1540. A controller 1510 can communicate with a memory 1512 via a bidirectional data bus. The memory 1512 can include read only memory (ROM) or random access memory (RAM) for program storage and RAM for data storage.

In some embodiments, a medical device can include one or more electric field sensors 1522 (i.e., electrodes) and an electric field sensor channel interface 1520 that can communicate with a port of controller 1510. The medical device can also include another type of sensor 1532 and a sensor channel interface 1530 for the same that can communicate with a port of controller 1510. The medical device can also include one or more chemical sensors 1542 and a chemical sensor channel interface 1540 that can communicate with a port of controller 1510. The channel interfaces 1520, 1530 and 1540 can include various components such as analog-to-digital converters for digitizing signal inputs, sensing amplifiers, registers that can be written to by the control circuitry to adjust the gain and threshold values for the sensing amplifiers, and the like. A telemetry interface 1514 is also provided for communicating with external devices such as a programmer, a home-based unit, and/or a mobile unit (e.g. a cellular phone, laptop computer, etc.).

In some embodiments, the medical device can also include additional sensors, such as posture sensors, activity sensors, or respiration sensors integral to the medical device. In some embodiments, the medical device can also include additional sensors that are separate from medical device. In various embodiments one or more of the posture sensors, activity sensors, or respiration sensors can be within another implanted medical device communicatively coupled to the medical device via telemetry interface 1514. In various embodiments one or more of the additional posture sensors, activity sensors, or respiration sensors can be external to the body and are coupled to medical device via telemetry interface 1514.

Battery Chemistries

In various embodiments herein, the electrochemical cell can be a primary lithium-manganese dioxide (Li anode/ $MnO_2$ cathode) battery. However, other primary lithium battery chemistries are also contemplated herein. Other primary battery chemistries can include, but are not limited to, CFx, SVO, hybrid CFx/Mn02, hybrid CFx/SVO, and the like.

In various embodiments, the lithium battery can be constructed from a number of thin sheets of different materials that are sandwiched together to form a battery assembly. A repeating arrangement within the cell can include an anode assembly, a separator, and a cathode. The anode assembly can be formed from a sheet of lithium material that constitutes an anode and a material that constitutes a current collector. A sheet of lithium material can be laminated to a substrate, such as a current collector. The current collector can be constructed from a number of different materials. For example, the current collector can be constructed from, among other alternatives, nickel or nickel-based material, stainless steel, aluminum, titanium, or copper, or any other suitable material. The current collector can include a uniform sheet, a wire grid, or other configurations. Further details of exemplary electrochemical cell components are described in U.S. Publ. Pat. Appl. Nos. 2008/0221629 and 2017/0317331, the content of which is herein incorporated by reference.

Various electrolyte compositions can be used with electrochemical cells or batteries herein. In some embodiments, the electrolyte can be non-aqueous (e.g., organic only electrolyte solvent). In some embodiments, the electrolyte is a 1M LiTFSi solution in ethylene carbonate, propylene carbonate and dimethoxy ethane. Various separators can be used with electrochemical cells or batteries herein.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An implantable medical device comprising:
    a power subunit comprising
        a first biocompatible electrically conductive shell configured for direct contact with an in vivo environment;
        a lithium anode disposed within the first biocompatible electrically conductive shell in direct electrical communication with a feedthrough pin, wherein the feedthrough pin is electrically isolated from the first biocompatible electrically conductive shell; and
        a cathode disposed within the first biocompatible electrically conductive shell;
        a lid for the power subunit;
        a cathode connection tab configured to provide electrical communication between the cathode, the lid, and the first biocompatible electrically conductive shell; and
    an electronics control subunit comprising
        a second biocompatible electrically conductive shell configured for direct contact with an in vivo environment;
        a control circuit disposed within the second biocompatible electrically conductive shell;
    wherein the power subunit is coupled to the electronics control subunit and the power subunit is in electrical communication with the electronics control subunit;
    wherein the first biocompatible electrically conductive shell has a positive electrical potential.

2. The implantable medical device of claim 1, the first biocompatible electrically conductive shell and the second biocompatible electrically conductive shell comprising titanium or a titanium alloy.

3. The implantable medical device of claim 1, wherein the first biocompatible electrically conductive shell comprises machined surfaces.

4. The implantable medical device of claim 1, wherein the first biocompatible electrically conductive shell comprises stamped surfaces.

5. The implantable medical device of claim 1, wherein the first biocompatible electrically conductive shell comprises an exterior surface for contact with an in vivo environment, the implantable medical device further comprising a polymeric coating disposed over a portion of the exterior surface of the first biocompatible electrically conductive shell.

6. The implantable medical device of claim 5, the polymeric coating comprising parylene.

7. The implantable medical device of claim 1, the first biocompatible electrically conductive shell having a thickness of 0.006 to 0.012 inches.

8. The implantable medical device of claim 1, wherein the first biocompatible electrically conductive shell has perimeter dimensions that are less than 5 percent different than the second biocompatible electrically conductive shell.

9. The implantable medical device of claim 1, wherein the first biocompatible electrically conductive shell and the second biocompatible electrically conductive shell are welded together.

10. The implantable medical device of claim 1, wherein the first biocompatible electrically conductive shell of the power subunit has an electrical potential of 2.5 V vs. lithium to 3.5 V vs. lithium.

11. An implantable medical device comprising:
    a power subunit comprising
        a first biocompatible electrically conductive shell configured for direct contact with an in vivo environment;
        a lithium anode disposed within the first biocompatible electrically conductive shell in direct electrical communication with a first feedthrough pin, wherein the first feedthrough pin is electrically isolated from the first biocompatible electrically conductive shell; and
        a cathode disposed within the first biocompatible electrically conductive shell and in direct electrical communication with the first biocompatible electrically conductive shell; and
    an electronics control subunit comprising
        a second biocompatible electrically conductive shell configured for direct contact with an in vivo environment;
        a control circuit disposed within the second biocompatible electrically conductive shell;
    wherein the power subunit is coupled to the electronics control subunit and the power subunit is in electrical communication with the electronics control subunit;
    wherein the first biocompatible electrically conductive shell of the power subunit has an electrical potential of between 0.2 to 0.5 V vs. lithium.

12. The implantable medical device of claim 11, wherein the first biocompatible electrically conductive shell comprises machined surfaces.

13. The implantable medical device of claim 11, wherein the first biocompatible electrically conductive shell comprises stamped surfaces.

14. The implantable medical device of claim 11, the first biocompatible electrically conductive shell having a thickness of 0.006 to 0.012 inches.

15. An implantable medical device comprising:
   a power subunit comprising
      a first biocompatible electrically conductive shell configured for direct contact with an in vivo environment;
      a lithium anode disposed within the first biocompatible electrically conductive shell in direct electrical communication with a first feedthrough pin, wherein the first feedthrough pin is electrically isolated from the first biocompatible electrically conductive shell; and
      a cathode disposed within the first biocompatible electrically conductive shell and in direct electrical communication with the first biocompatible electrically conductive shell; and
   an electronics control subunit comprising
      a second biocompatible electrically conductive shell configured for direct contact with an in vivo environment;
      a control circuit disposed within the second biocompatible electrically conductive shell;
   wherein the power subunit is coupled to the electronics control subunit and the power subunit is in electrical communication with the electronics control subunit;
   the electronic control subunit comprising a negative bias output pin;
   the implantable medical device further comprising an electrical conductor providing electrical communication between the negative bias output pin and the first biocompatible electrically conductive shell;
   wherein the first biocompatible electrically conductive shell has an electrical potential greater than 0.001 V vs lithium and less than 3.0 V vs lithium.

16. The implantable medical device of claim 15, wherein the first biocompatible electrically conductive shell has an electrical potential greater than 0.1 V vs lithium and less than 3.0 V vs lithium.

17. The implantable medical device of claim 15, wherein the first biocompatible electrically conductive shell comprises machined surfaces.

18. The implantable medical device of claim 15, wherein the first biocompatible electrically conductive shell comprises an exterior surface for contact with an in vivo environment, the implantable medical device further comprising a polymeric coating disposed over a portion of the exterior surface of the first biocompatible electrically conductive shell.

19. The implantable medical device of claim 15, the first biocompatible electrically conductive shell having a thickness of 0.006 to 0.012 inches.

* * * * *